United States Patent [19]

Handjani et al.

[11] Patent Number: 4,830,857

[45] Date of Patent: May 16, 1989

[54] COSMETIC AND PHARMACEUTICAL COMPOSITIONS CONTAINING NIOSOMES AND A WATER-SOLUBLE POLYAMIDE, AND A PROCESS FOR PREPARING THESE COMPOSITIONS

[75] Inventors: Rose M. Handjani; Alain Ribier, both of Paris; Guy Vanlerberghe, Villevaude; Arlette Zabotto, Paris; Jacqueline Griat, Ablon, all of France

[73] Assignee: The French Joint Stock Company "L'Oreal", Paris, France

[21] Appl. No.: 789,775

[22] Filed: Oct. 21, 1985

[30] Foreign Application Priority Data

Oct. 24, 1984 [FR] France .................. 84 16312

[51] Int. Cl.⁴ ................ A61K 7/48; A61K 9/58
[52] U.S. Cl. .................... 424/450; 424/417; 264/4.1; 264/4.6; 428/402.2
[58] Field of Search ........... 424/450, 417; 264/4.1, 264/4.3, 4.6; 428/402.2

[56] References Cited

U.S. PATENT DOCUMENTS

| | | | |
|---|---|---|---|
| 4,217,344 | 8/1980 | Vanlerberghe et al. | 264/4.1 |
| 4,409,201 | 10/1983 | Heinrich et al. | 264/4.1 |
| 4,608,211 | 8/1986 | Handjani et al. | 264/4.6 |

FOREIGN PATENT DOCUMENTS

| | | |
|---|---|---|
| 0120722 | 10/1984 | European Pat. Off. . |
| 2532191 | 3/1984 | France . |
| 2079179 | 1/1982 | United Kingdom . |
| 2136762 | 9/1984 | United Kingdom . |

OTHER PUBLICATIONS

English language abstract of EPO 0120722 (10-3-84).
Chemical Abstracts, vol. 96, No. 18, May 1982, p. 422, No. 149167z.
Formulations of antiinflammatory steroid-containing liposomes.

*Primary Examiner*—John Kight
*Assistant Examiner*—Nathan M. Nutter
*Attorney, Agent, or Firm*—Cushman, Darby & Cushman

[57] ABSTRACT

The invention relates to a composition consisting of a dispersion in an aqueous medium D of niosome and/or liposome spherules, within which an aqueous phase E is encapsulated, at least one portion of the spherules being niosomes; the lipids forming spherules constituting from 2 to 10% of the weight of the composition; in at least one of the phases E and D there is dissolved at least one water-soluble polyamide polymer having a molecular weight between 1,000 and 200,000, at a concentration of 0.01 to 5% by weight relative to the total weight of the composition. Usable in cosmetics or pharmaceuticals.

30 Claims, No Drawings

COSMETIC AND PHARMACEUTICAL COMPOSITIONS CONTAINING NIOSOMES AND A WATER-SOLUBLE POLYAMIDE, AND A PROCESS FOR PREPARING THESE COMPOSITIONS

The present invention relates to a composition consisting of an aqueous dispersion of lipid spherules which contain a water-soluble polyamide polymer; such a composition is usable in the cosmetic and pharmaceutical fields.

By water-soluble polyamide polymer, there is understood both a natural polymer and a synthetic polymer.

In French Pat. No. 2,315,991, dispersions of lipid spherules have already been described; these spherules are characterised by their lamellar structure consisting of two or more lipid layers separated from each other by layers of aqueous phase; they can thus serve to encapsulate, in the aqueous compartments between the lipid layers, water-soluble active substances, for example pharmaceutical or cosmetic substances, and to protect them from the external conditions. The abovementioned French Patent also describes a process for preparing these dispersions. The lipid compostions which can be used to form such spherules can be ionic compounds, in which case liposomes are obtained, or nonionic compounds, in which case niosomes are obtained.

In French Pat. Nos. 2,485,921 and 2,490,504, compositions have also been described which consist of an aqueous dispersion of spherules of the abovementioned type in the external aqueous phase, from which compositions an oil dispersion was provided. It was found, surprisingly, that the presence of the lipid spherules enabled the oil dispersion to be stabilised, and in addition that, with such compositions, a combined effect of the spherules and the oil droplets was obtained, which had a substantial advantage in the field of cosmetics or pharmaceuticals.

In French patent application No. 83/04674, a process was proposed for preparing unilamellar lipid vesicles having an average diameter greater than 1000 Angstroms, enabling glucose or protein derivatives to be encapsulated.

It has already been noted that the behaviour of liposomes in the aqueous medium in which they are dispersed is very strongly influenced by the presence of various proteins (in this connection, see the article "Interactions of liposomes with plasma proteins and components of the immune system" by Gerrit Scherphof, Jan Damen and Dick Hoekstra, published in pages 299–322 in the work "Liposomes: From physical structure to therapeutic applications", 1981). The same phenomenon has been demonstrated between liposomes and polyethylene glycol [see paper by Boni, Stewart, Alderfer and Hui, J. Membrane Biol. 62, pages 65–70 (1981)]. Since liposomes consist of ionic lipid, the interactions demonstrated in the above-mentioned publications take place through ionic bonding, and this causes considerable damage to the spherules, resulting in at least partial loss of the encapsulated aqueous phase and, in certain instances, even in complete destruction of the spherules. Hitherto, the behaviour of niosomes in the presence of proteins or polymers has not yet been studied in detail.

According to the invention, the Applicant Company has found that, in contrast to what might be feared, the interaction between certain proteins or certain polymers, on the one hand, and the niosomes on the other hand had a far less destructive effect than the effects observed in the state of the art with liposomes. It was, however, found that not all polymers gave rise to a favourable level of interaction and that, to benefit from a significant interaction effect, it was desirable that the polymer should contain amide groups. It was noted, according to the invention, that the concentration of the polymer in the aqueous medium in which it is dissolved, the method of incorporation thereof in the spherule dispersion and the choice of structure of the polymer are parameters which modulate the interaction and, consequently the properties of the dispersions obtained. The polymer is dissolved in the aqueous medium external to the spherules: its interaction with the lipid molecules forming the layers of the spherules consequently takes place on the external polar heads of these layers.

Since the lipid leaves of the niosomes consist of nonionic lipids, there are, between the polymer and the spherules, only interactions of the hydrogen bond type, by virtue of the presence of hydroxyl groups on the nonionic lipid molecule, or Van der Waals type forces. However, according to the parameters mentioned above, interactions of greater or lesser intensity are obtained, and these can be turned to account according to the desired objectives.

A polymer/niosome interaction of low intensity will result in a change in the rheological behaviour of the dispersion, with some gathering of the vesicles in the preparation; a reduction in viscosity, lessening as the interaction becomes weaker, may be noted. In contrast, in the case of a polymer/niosome interaction of high intensity, it is possible to observe precipitation of the spherules within the sample, which can be turned to account to purify the niosome dispersions, or even coalescence of the spherules, which can be turned to account for producing large aqueous vacuoles with a high degree of encapsulation, this being especially desirable for therapeutic applications.

In the case of a polymer/niosome interaction of moderate intensity, coating of the spherules by the polymer molecules is observed without the phenomenon of fusion or precipitation, and this enables the spherules to be endowed with different affinities for biological membranes or tissues by an appropriate choice of the coating polymer.

From the known polymer/liposome interactions, it was not possible to predict the interactions with niosomes. By way of example, it can be pointed out that, from the experiments performed, polyethylene glycol showed no interaction with niosomes while it shows a very strong interaction with liposomes. It scarcely seemed to be possible to predict the intensity of the interaction between a polymer and a niosome, since this interaction depends on the structure of the polymer and the distribution of molecular weights. It can, however, be pointed out, by way of examples, that some collagen hydrolysates ("Nutrilan 1" of molecular weight equal to approximately 1000, "Colamar") and some gelatin hydrolysates ("Crotein C" of molecular weight equal to approximately 10,000) showed a strong interaction; poly-beta-alanine showed a moderate interaction; some polysaccharides ("Dextran T 70") and polyacrylamide showed a weak interaction; and polyvinyl-pyrrolidone, polyvinyl alcohol, polyethylene glycol, some collagen hydrolysates ("Lexein×300" of molecular weight equal to approximately 1000) and some lactic hydrolysates ("Permeate GR 6 P" of molecular weight ≃1000) showed no interaction.

The polymers according to the invention must, like poly-beta-alanine, show an interaction with niosomes which is neither too strong nor too weak. Thus, according to the invention, it has been found that it was possible to benefit from a significant interaction, which could be used favourably from a technical standpoint, by bringing together with the niosomes a water-soluble poly-amide polymer having a molecular weight between 1000 and 200,000. In the context thereby defined for the invention, several possible consequences of the polymer/niosome interactions have been observed:

(a) In certain cases, the presence of polymer enables the size of the spherules to be increased, and this can be advantageous for preventing the passage of the spherules through the skin; thus, the preparation of niosomes in the presence of a solution of poly-beta-alanine having a molecular weight of approximately 90,000 enables spherules to be obtained having a diameter of 1,150 nanometres, whereas the spherules obtained in the same manner but in the absence of polymer have a diameter of 650 nanometres; now, it is advantageous to have available spherules of large size to improve the encapsulation yield.

(b) In other cases, the presence of the polymer enables the rheology of the niosome dispersions to be modified; thus, the addition to a niosome dispersion of an aqueous solution containing 1.5% by weight of poly-beta-alanine causes a decrease of one half in the viscosity of the dispersion, measured with a "Deer" rheometer with a stress rate of $5 \times 10^{-1}$ N/m$^2$ (the viscosity drops from 10 cP to 5 cP).

(c) In yet other cases, the presence of polymer can affect the diffusion of the niosomes in biological tissues or membranes; thus, if a dispersion of niosomes in aqueous solution or in aqueous solution containing 1.5% by weight of poly-beta-alanine is used for treating the skin of a subject, a change of 10% in the modulus of elasticity of the treated stratum corneum is noted among the effects of the treatment.

(d) In the case of using poly-beta-alanine as a polymer in combination with the niosomes, it has been found that the presence of the polymer causes a decrease in the membrane viscosity of the niosomes, which then attains a value close to that of the erythrocyte membrane, and this enables the use of such dispersions, encapsulating a haemoglobin solution, to be envisaged as a blood substitute.

It is specified that the poly-beta-alanine mentioned in the present application corresponds to the definition of polymer which is given in Claim 1 of Belgian Pat. No. 893,738 in the name of the Applicant Company.

It consequently follows from the explanations given above that the presence of a polymer which interacts with the lipid compounds forming the niosomes makes it possible in particular to influence the adsorption of the spherules onto cell surfaces, to influence the pharmacokinetics of treatment products encapsulated in the niosomes, and to avoid the possible interactions between the niosomes and the plasma proteins or the components of the immune system when the niosomes are injected into the blood circulatory system.

The subject of the present invention is consequently the new industrial product constituted by a composition, for cosmetic or pharmaceutical use, consisting of a dispersion in an aqueous medium D of spherules composed of organised layers of lipid molecules, within which layers an internal aqueous phase E is encapsulated, at least a part of the said spherules being formed from layers consisting of at least one nonionic amphiphilic lipid, the lipid or lipids which form(s) the organised layers of the said spherules constituting 2 to 10% by weight of the total weight of the composition, characterised in that, in the aqueous phase D there is dissolved at least one water-soluble polyamide polymer having a molecular weight of between 1000 and 200,000, the concentration of which is from 0.01% to 5% by weight relative to the total weight of the composition.

The relative proportion by weight of nonionic amphiphilic lipid or lipids forming the walls of the spherules, with respect to the polyamide polymer or polymers, is advantageously between 100 and 1.

The polymers dissolved in the aqueous phase D of the composition according to the invention can be either synthetic polyamides or proteins. If these polymers are synthetic polyamides, they are advantageously chosen from the group consisting of polyacrylamide, poly-beta-alanine, poly(glutamic acid), polytyrosine, polylysine and poly(aspartic acid); for the implementation of the invention, the preferred polymer is poly-beta-alanine. In the case where, on the other hand, the polymers dissolved in the aqueous phase D of the composition according to the invention are proteins, the latter are advantageously chosen from the group consisting of α-lactalbumin, serum albumin, lactic hydrolysates, collagen hydrolysates and gelatin hydrolysates.

In a first variant, all the spherules in the composition according to the invention are niosomes. In a second variant, these spherules consist, on the one hand of niosomes and on the other hand of liposomes, the ionic lipids constituting at most 90% of the lipids which form spherules.

When multilamellar spherules are used, it is preferable to use spherules having an average diameter between 1,000 and 50,000 Å, such as those described in French Pat. No. 2,315,991. When unilamellar spherules are used, it is preferable to use those of diameter greater than 1,000 Å, the process for production of which is described in French patent application No. 83/04674.

The lipids forming the spherules of the composition according to the invention preferably have a lipophile/hydrophile ratio such that the lipid swells in the aqueous phase to form a lamellar phase, the lipophilic groups of the said lipids consisting of a chain containing from 12 to 30 carbon atoms. These lipids are advantageously chosen from those containing an oleic, lanolic, tetradecyl, hexadecyl, isostearyl, lauric or alkylphenyl chain.

For the nonionic lipid compounds forming spherules in the composition according to the invention, it is preferred that the hydrophilic groups are polyoxyethylenated or polyglycerolated groups, or groups derived from polyol esters which may or may not be oxyethylenated. Advantageously, these nonionic lipid compounds are chosen from the group consisting of:

Linear or branched polyglycerol ethers of respective formulae:

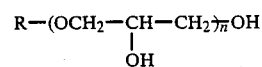

and

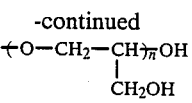

n being an integer between 1 and 6, and R being a saturated or unsaturated linear or branched aliphatic chain containing from 12 to 30 carbon atoms, the hydrocarbon radicals of lanolin alcohols or the 2-hydroxyalkyl residues of long-chain alpha-diols;
  polyoxyethylenated fatty alcohols;
  polyoxyethylenated sterols;
  polyol esters which may or may not be oxyethylenated, and especially polyoxyethylenated esters of sorbitol;
  glycolipids of natural or synthetic origin, for example cerebrosides.

In the case where the composition according to the invention contains liposomes having an ionic hydrophilic group, the said hydrophilic group is advantageously derived from an amphoteric compound containing two lipophilic chains or a combination of two long-chain organic ions of opposite signs.

In a known manner, various additives may be combined with the lipid compounds, for the purpose of modifying the permeability or surface charge of the spherules. In this connection, there will be mentioned the possible addition of long-chain alcohols and diols, of sterols, for example cholesterol and β-sitosterol, of long-chain amines and their quaternary ammonium derivatives, of hydroxy-alkyl-amines, of polyoxyethylenated fatty amines, of long-chain amino alcohol esters, their salts and quaternary ammonium derivatives, of phosphoric esters of fatty alcohols, for example sodium dicetyl phosphate, of alkyl sulphates, for example sodium cetyl sulphate, and of ionic derivatives of sterols, for example cholesterol sulphate or phosphate.

Provision can be made for the aqueous phase E, which is to be encapsulated within the spherules, to be an aqueous solution of active substance, preferably isoosmotic with respect to the phase D of the dispersion. The aqueous phase E may contain various products in solution, in particular polymers. For a cosmetic composition, the aqueous phase E encapsulated within the spherules contains, for example, at least one product chosen from the group consisting of humectants such as glycerine, sorbitol, pentaerythritol, inositol, pyrrolidone-carboxylic acid and its salts; artificial suntanning agents such as dihydroxyacetone, erythrulose, glyceraldehyde, alpha-dialdehydes such as tartaric aldehyde, optionally combined with colorants; water-soluble agents for protection against sunlight; antiperspirants, deodorants; astringents; freshening agents, tonics, healing, keratolytic and depilatory products; animal or plant tissue extracts; perfumed waters; water-soluble colorants; anti-dandruff agents; antiseborrheic agents; oxidising agents such as hydrogen peroxide and reducing agents such as thioglycolic acid and its salts.

In the case of the composition according to the invention which can be used as a pharmaceutical, the aqueous phase E encapsulated within the spherules preferably contains at least one product selected from the group consisting of vitamins, hormones, enzymes such as superoxide dismutase, vaccines, anti-inflammatories such as hydrocortisone, antibiotics and bactericides.

According to an advantageous characteristic of the composition according to the invention, provision can be made for the aqueous phase D surrounding the spherules to contain at least one liquid phase immiscible with water and dispersed in the said aqueous phase D. This liquid phase immiscible with water can be an oil or a constituent selected from the group consisting of hydrocarbons, halogenated hydrocarbons, polysiloxanes, inorganic acid esters, ethers and polyethers. Advantageously, the amount of liquid phase immiscible with water, dispersed in the aqueous phase D, is between 2 and 40% by weight relative to the total weight of the composition, the relative proportion by weight of amphiphilic lipid constituting spherules relative to the dispersed liquid phase or phases immiscible with water, being between 0.2 and 1.

The oil used for the purpose of dispersion in the aqueous phase D is advantageously selected from the group consisting of esters of fatty acids and polyols, in particular liquid triglycerides, and esters of fatty acids and branched alcohols of formula R—COOR', in which formula R denotes the residue of a higher fatty acid containing from 8 to 20 carbon atoms and R' denotes a branched hydrocarbon chain containing from 3 to 20 carbon atoms. In such a case, if the oil is an ester of a fatty acid and polyol, it is preferably chosen from the group consisting of sunflower, maize, soya, pumpkin, grape pip and jojoba oils and glycerol tricaprocaprylate; if, on the other hand, the oil is an ester of a higher fatty acid and a branched alcohol, it is preferable that the said oil should be purcellin oil.

To constitute the liquid phase immiscible with water, hexadecane, liquid paraffin, perhydrosqualene, perfluorotributylamine and perfluorodecahydronaphthalene can also advantageously be chosen.

Provision can also be made for the aqueous phase D, which surrounds the spherules, to contain at least one adjuvant selected from the group consisting of opacifiers, gelifying agents, aromas, perfumes, sunscreens and colorants, those among these adjuvants which are lipid-soluble being able to be dissolved in the liquid phase immiscible with water, dispersed in the aqueous phase D in the case where a dispersion of this kind is used.

To prepare the cosmetic or pharmaceutical compositions according to the present invention, which contain the polymer in the phase D, a dispersion of spherules can, in a first phase, be prepared according to the processes described in French Pat. Nos. 2,221,122 and 2,315,991 or French patent application No. 83 04674.

In a second phase, the polymer is added to the aqueous phase D, mixing being accomplished by vigorous mechanical agitation, preferably at a temperature between 10° and 50° C.

In an optional third phase, if it is desired to add a dispersion of liquid or liquids immiscible with water to the aqueous phase D, this/these liquid/liquids is/are introduced into the continuous aqueous phase which surrounds the spherules, and the mixture is agitated to obtain the dispersion as described in French Pat. No. 2,485,921. The agitation indicated for the second phase can be eliminated and replaced by that of the third phase, when one or more liquids immiscible with water is/are added to the phase D.

Naturally, if the aqueous phase external to the spherules has to contain adjuvants, the said adjuvants can be introduced before, after or at the same time as the polymer; if the dispersed liquid immiscible with water, added in the last stage, has to contain dissolved adjuvants, the dissolution of these adjuvants is carried out before the dispersion is performed.

When a composition containing a dispersion of liquid or liquids immiscible with water is produced, it is found that this dispersion is stable without using an emulsifier, leading to an oil-in-water emulsion.

If the dispersion of spherules contains spherules of several types, for example niosomes and liposomes, the two types of spherules are prepared separately and the two dispersions are mixed, preferably before dissolving the water-soluble polyamide polymer.

In the case where the composition according to the invention is produced using multilamellar spherules, the preparation process as described in French Pat. No. 2,315,991 is preferably used: thus, to obtain the spherule dispersion, on the one hand at least one lipid intended for formation of the layers of the spherules, and on the other hand the aqueous phase E to be encapsulated, are brought into contact, the ratio of the lipophilic portion/hydrophilic portion of the lipid being such that the latter swells in the aqueous phase to be encapsulated, to form a lamellar phase; the mixture is agitated to ensure that mixing takes place and to obtain a lamellar phase; the dispersion liquid D is added in a greater amount than the amount of lamellar phase obtained; and the mixture is shaken vigorously for a time varying from about 15 minutes to 3 hours.

In the case where it is desired to use unilamellar spherules, the process described in French patent application No. 83/04674 is preferably used for the preparation thereof: thus, the lipid or lipids intended for formation of the leaf of the vesicles may be solubilised in at least one solvent insoluble in water; the lipid solution is packaged in the liquid state in a container at a pressure $P_1$ and at a temperature $\ominus_1$; the aqueous phase to be encapsulated E is packaged at a pressure $P_2$ and at a temperature $\ominus_2$, and the lipid solution is injected into the aqueous phase in such a manner that the solvent or solvents in the lipid solution vaporise(s) when it/they come/comes into contact with the said aqueous phase, the said injection being performed at a low rate of flow to form the droplets initially, the pressure $P_2$ being less than $P_1$ and than the vapour pressure of the solvent or solvents in the said droplets at the temperature $\ominus_2$.

To enable the subject of the invention to be more readily understood, several embodiments thereof will now be described by way of examples which are purely illustrative and not limitative.

EXAMPLE 1

Skin care fluid for dry skin

In a first phase, the process described in French Pat. No. 2,315,991 was used to obtain a niosome dispersion from the following formulation:

nonionic amphiphilic lipid of formula:

$$R+OCH_2-CH \xrightarrow{}_n OH \qquad 3.8 \text{ g}$$
$$| \qquad \qquad CH_2OH$$

in which R is a hexadecyl radical and n has an average statistical value equal to 3.

| | |
|---|---|
| Cholesterol | 3.8 g |
| Dicetyl phosphate | 0.4 g |
| Methyl para-hydroxybenzoate (stabiliser) | 0.3 g |
| Glycerine | 3.0 g |
| Demineralised water | 35.5 g |

A niosome dispersion having an average diameter of 10,000 Angstroms is obtained.

In a second phase, 7 g of aqueous solution of poly-β-alanine having a molecular weight of approximately 50,000, the solution containing 20% of active material, are added to the aqueous dispersion obtained in the first phase.

In a third phase, 25 grams of sesame oil are added to the mixture thereby obtained. The whole mixture is subjected to mechanical agitation until the external phase of the dispersion forms an oil-in-water emulsion.

The following substances are then added:

| | |
|---|---|
| Perfume | 0.4 g |
| Polyvinylcarboxylic acid marketed under the name "Carbopol 940" | 0.4 g |
| Triethanolamine | 0.4 g |
| Demineralised water | 20.0 g |

The skin care fluid thereby prepared was tested by performing comparative trials on forty people having dry skin; a comparison was made between the skin care fluid described in the present example and a composition identical except that the quantity of poly-beta-alanine was replaced by water. The conclusions of the medical expert show that, in the presence of poly-beta-alanine, the product is more effective (100% improvement in the clinical state of the skin of the treated subjects) and better tolerated (no case of intolerance).

EXAMPLE 2

Skin care fluid for aged skin

In a first phase, two dispersions of spherules were separately prepared, one of them containing niosomes and the other liposomes.

The niosome dispersion was obtained by employing the process described in French Pat. No. 2,315,991, with the following formulation:

Nonionic amphiphilic lipid of formula:

$$R+O-CH_2-CH \xrightarrow{}_n OH \qquad 1.9 \text{ g}$$
$$| \qquad \qquad CH_2OH$$

in which R is a hexadecyl radical and $\bar{n}$ has an average statistical value equal to 3.

| | |
|---|---|
| Cholesterol | 1.9 g |
| Dicetyl phosphate | 0.2 g |
| Methyl para-hydroxybenzoate (stabiliser) | 0.15 g |
| Hydroxyproline | 0.7 g |
| Demineralised water | 21.4 g |

The niosomes obtained have an average diameter of 10,000 Angstroms.

The same preparation process is used to manufacture a liposome dispersion from the following formulation:

| | |
|---|---|
| Soya lecithin Epikuron E200 product marketed by Lukas Meyer | 3.3 g |
| Dicetyl phosphate | 0.2 g |
| DL-α-tocopherol | 0.25 g |
| Linoleic acid | 0.25 g |
| Methyl para-hydroxybenzoate (stabiliser) | 0.15 g |
| Demineralised water | 21.4 g |

The liposomes in the dispersion have an average diameter of approximately 5,000 Angstroms.

The two dispersions thereby obtained are mixed.

In a second phase, 7 g of an aqueous solution containing 20% by weight of collagen proteins having a molecular weight of approximately 1,000, marketed under the name "Nutrilan 1" by CRODA, were added to the mixture thereby prepared.

In a third phase, 20 g of sweet almond oil are added to the mixture prepared above. The whole mixture is subjected to mechanical agitation until the external phase of the dispersion forms an oil-in-water emulsion.

The following substances are then added:

| | |
|---|---|
| Perfume | 0.4 g |
| Polyvinylcarboxylic acid marketed under the name "Carbopol 940" | 0.4 g |
| Triethanolamine | 0.4 g |
| Demineralised water | 20.0 g |

It is found that this skin care fluid, used in topical application once daily on elderly subjects, gives satisfactory results after 30 days' application. If the same fluid is prepared without the collagen proteins being introduced, significantly reduced efficacy is observed.

EXAMPLE 3

Blood substitute

In a first phase, a dispersion of unilamellar spherules was prepared by employing the process described in French patent application No. 83/04674.

In a 150 ml aerosol container, there is introduced 0.5 g of a lipid mixture corresponding to the following formulation: Nonionic lipid compound of general formula:

   47.5% by weight in which R is a hexadecyl radical and $\bar{n}$ has an average statistical value equal to 3.

| | |
|---|---|
| Cholesterol | 47.5% |
| Dicetyl phosphate | 5% |

100 g of trichlorofluoromethane are added into the aerosol container and the container is crimped so as to seal it. 4 g of nitrous oxide are introduced into the container.

The microvalve transfer device shown in FIG. 2 of French patent application No. 83/04674 is connected to the aerosol container; the distribution capillary is immersed in 50 ml of 15% concentration aqueous haemoglobin solution present in a flat-bottomed Erlenmeyer type container equipped with a vacuum take-off. A bar magnet is introduced in the haemoglobin solution and the Erlenmeyer is placed in a water bath thermostatted at 20° C. on a magnetic stirrer. Pressure of 15 mbar is established in the Erlenmeyer by means of a filter pump. The microvalve is adjusted to obtain a flow rate of 3 ml/min from the aerosol container into the haemoglobin.

An aqueous dispersion of spherules is thereby obtained, and this is subjected to a reduced pressure of 0.1 mbar for one hour in order to drive off the last traces of solvent. The average size of the unilamellar spherules thereby obtained is approximately 300 nanometres.

The aqueous dispersion of spherules is subjected to centrifugation for one hour at 14,000 rpm; the spherule pellet is recovered and redispersed with 15 ml of aqueous physiological saline solution; this centrifugation/redispersion procedure is repeated twice in order to remove all traces of free haemoglobin.

In a second phase, after a further centrifugation, the spherule pellet is redispersed in 8 ml of physiological saline containing 0.1 g of poly-β-alanine having a molecular weight of approximately 50,000.

In a third phase, 2 g of perfluorodecahydronaphthalene are added and the whole mixture is subjected for ten minutes to the agitation produced by a "VIRTIS" ultradispersant at a speed of 30,000 rpm. A fluid is thereby obtained which can serve as a blood substitute.

EXAMPLE 4:

Anti-inflammatory composition for topical application.

In a first phase, two dispersons of sperules are prepared, one containing niosomes and the other liposomes. The dispersion of niosomes was obtained by carrying out the process described in French Pat. No. 2,315,991 with the following formulation:- nonionic amphiphilic lipid of formulae:

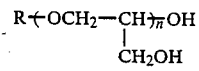

(in which R is a hexadecyl radical and $\bar{n}$ has an average statistical value equal to 3)

| | |
|---|---|
| Cholesterol | 1.9 g |
| Dicetyl phosphate | 1.9 g |
| | 0.2 g |
| Chlorhexidine gluconate | 0.15 g |
| Demineralised water | 22.1 g |

The niosomes obtained have an average diameter of 10,000 Å. The same process is employed to manufacture a disperson of liposomes starting from the following formulation:

| | |
|---|---|
| Soya lecithin (Epikuron E200 marketed by Lukas Meyer) | 3.3 g |
| Dicetyl phosphate | 0.2 g |
| Hydrocortisone reagent marketed by IBF) | 0.2 g |
| Methyl para-hydroxybenzoate | 0.15 g |
| Demineralised water | 21.4 g |

The liposomes in the disperson have an average diameter of 5,000 Å.

The two dispersons thereby obtained are mixed together.

In a second phase, there are added to the mixture thereby prepared 7 g of an aqueous solution containing 20% by weight of collagen proteins having a molecular weight of approximately 1,000, marketed under the name "Nutrilan I" by Croda.

In a third phase, there are added to the previously prepared mixture 10 g of Codex vaseline, mixed beforehand with 15 g of perhydrosqualene, on a water-bath maintained at 60° C. The whole mixture is subjected to mechanical agitation until the external phase of the dispersion forms an oil-in-water emulsion. After cooling, an ointment is thereby obtained which is intended for skin affected by psoriasis.

EXAMPLE 5:

Composition for oral administration.

In a first phase, a disperson of niosomes is prepared by carrying out the process described in French Pat. No. 2,315,991 with the following formulation:
Nonionic amphiphilic lipid of the formula,

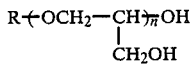

(in which R is a hexadcyl radical and n has an average statistical value equal to 3)

|  |  |
| --- | --- |
| Cholesterol | 1.9 g |
| Dicetyl phosphate | 1.9 g |
| 5% strength aqueous solution of IgA immunoglobulins | 0.2 g q.s. 100 g |

The niosomes obtained have an average diameter of 10,000 Å. The disperson of niosomes is subjected to centrifugation for 1 hour at 18,000 rpm. The spherule pellet obtained is lyophilised.

In a second phase, the spherule lyophilisate is resuspended in 100 ml of a sultion of physiological saline containing 1 g of αlactalbumin.

In this way a disperson is obtained which can be administered orally to subjects suffering from immunodeficiency.

We claim:

1. A composition comprising a dispersion in an aqueous medium of spherules composed of one or more organized layers of lipid molecules, within which layers an internal aqueous phase is encapsulated, at least a part of said spherules being formed from layers consisting of at least one nonionic amphiphilic lipid, said lipid forming said organized layers of said spherules constituting 2 to 10 percent by weight of the total weight of the composition, wherein in said aqueous medium there is dissolved poly-beta-alanine having a molecular weight of between 1,000 and 200,000, the concentration of which is from 0.01 to 5 percent by weight relative to the total weight of the composition.

2. The composition of claim 1 wherein the relative proportion by weight of said nonionic amphiphilic lipid forming the walls of said spherules relative to said poly-beta-alanine is between 100 and 1.

3. The composition of claim 1 wherein said spherules are entirely niosomes.

4. The composition of claim 1 wherein spherules consist of nonionic lipids forming niosomes and ionic lipids forming liposomes.

5. The composition of claim 1 wherein said lipid forming said spherules has a lipophile/hydrophile ratio such that said lipid swells in said aqueous phase to form a lamellar phase, each lipophilic group of said lipid consisting of a chain containing from 12 to 30 carbon atoms.

6. The composition of claim 1 wherein said nonionic lipid forming said spherules has a hydrophilic group selected from the group consisting of a polyoxyethylenated group, a polyglycerolated group, a polyol ester group and an oxyethylenated polyol ester group.

7. The composition of claim 6 wherein said nonionic lipid forming said spherules is selected from the group consisting of
   (1) linear or branched polyglycerol ethers of respective formulae:

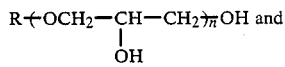

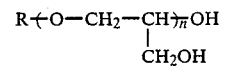

wherein n is an integer between 1 and 6, and R is a saturated or unsaturated linear or branched aliphatic chain containing from 12 to 30 carbon atoms, the hydrocarbon radicals of lanolin alcohols or the 2-hydroxyalkyl residues of long-chain alpha-diols,
   (2) polyoxyethylenated fatty alcohols,
   (3) polyoxyethylenated sterols,
   (4) polyol esters,
   (5) oxyethylenated polyol esters and
   (6) glycolipids of natural or synthetic origin.

8. The composition of claim 7 wherein said nonionic lipid forming said spherules is a polyoxyethylenated ester of sorbitol.

9. The composition of claim 1 which also includes at least one of a long-chain alcohol or diol, a sterol, a long-chain amine or quaternary ammonium derivative thereof, a hydroxyalkylamine, a polyoxyethylenated fatty amine, a long-chain amino alcohol ester or a salt or quaternary ammonium derivative thereof, a phosphoric ester of a fatty alcohol, an alkyl sulphate or an ionic derivative of a sterol.

10. The composition of claim 1 wherein said aqueous phase encapsulated within said spherules is an aqueous solution of a cosmetically or pharmaceutically active substance.

11. The composition of claim 10 wherein the encapsulated aqueous phase is isoosmotic with respect to the phase which surrounds said spherules.

12. The composition of claim 1 wherein the aqueous phase surrounding said spherules contains at least one liquid phase immiscible with water and dispersed in said aqueous phase.

13. The composition of claim 12 wherein the amount of liquid phase immiscible with water is between 2 and 40 percent by weight relative to the total weight of said composition and the relative proportion by weight of amphiphilic lipid constituting said spherules relative to said dispersed liquid phase immiscible with water is between 0.2 and 1.

14. The composition of claim 12 wherein said dispersed liquid phase immiscible with water is an oil, a hydrocarbon, a halocarbon, a polysiloxane, an inorganic acid ester, an ether or a polyether.

15. The composition of claim 14 wherein said oil is selected from the group consisting of an ester of a fatty acid and a polyol and an ester of a fatty acid and a branched alcohol having the formula R—COOR' wherein R is a residue of a higher fatty acid containing 8 to 20 carbon atoms and R' is a branched hydrocarbon chain containing 3–20 carbon atoms.

16. The composition of claim 14 wherein said dispersed liquid phase immiscible with water is hexadecane, liquid paraffin, perhydrosqualene, perfluorotributylamine or perfluorodecahydronaphthalene.

17. The composition of claim 1 for use in cosmetics wherein said aqueous medium in which said spherules are dispersed also includes an opacifier, a gelifying agent, an aroma, a perfume, a sunscreen or a colorant.

18. The composition of claim 1 for use as a cosmetic wherein said internal aqueous phase contains a humectant, artificial suntanning agent, water-soluble agent for protection against sunlight, antiperspirant, deodorant, astringent, freshening product, tonic product, healing product, keratolytic product, depilatory product, perfumed water, water-soluble colorant, anti-dandruff agent, antiseborrheic agent, oxidizing agent, reducing agent or an extract from animal or plant tissues.

19. The composition of claim 1 for use as a pharmaceutical wherein said internal aqueous phase contains a vitamin, hormone, enzyme, vaccine, anti-inflammatory agent, antibiotic or bactericide.

20. A process for preparing a composition according to claim 1 comprising:
in a first stage preparing a dispersion in an aqueous medium of spherules composed of one or more organized layers of lipid molecules, within which layers an internal aqueous phase is encapsulated, at least a part of said spherules being formed from layers consisting of at least one nonionic amphiphilic lipid, the lipid which forms the organized layers of said spherules constituting from 2 to 10 percent by weight of the total weight of the composition, and
in a second stage adding said poly-beta-alanine to form the aqueous phase surrounding said spherules, and mixing by vigorous mechanical agitation.

21. The process of claim 20 which includes, after adding said poly-beta-alanine and before mixing, the step of adding a liquid immiscible with water.

22. The process of claim 21 wherein said liquid immiscible with water contains a dissolved adjuvant.

23. The process of claim 20 wherein said agitation is carried out at a temperature ranging from 10° C. to 50° C.

24. The process of claim 20 for the preparation of a composition in which the aqueous phase surrounding said spherules contains an adjuvant, said process comprising introducing said adjuvant before, after or at the same time as said poly-beta-alanine is added.

25. The process of claim 20 wherein the dispersion of spherules contains a plurality of different types of spherules and said process comprises separately preparing each type of spherule dispersion and thereafter mixing together said separately prepared dispersions.

26. The process of claim 25 wherein the separately prepared dispersions are mixed prior to adding said poly-beta-alanine.

27. The process of claim 20 for preparing a composition comprising multilamellar spherules, said process comprising in said first stage contacting said lipid intended for the formation of the layers of said spherules with the aqueous phase to be encapsulated within said spherules, the ratio of the lipophilic portion/hydrophilic portion of said lipid being such that the latter swells in the said aqueous phase to be encapsulated so as to form a lamellar phase, agitating the resulting mixture such that mixing takes place and a lamellar phase is obtained, adding the aqueous dispersion medium in an amount greater than the amount of lamellar phase obtained and vigorously shaking the mixture for a period of time ranging from about 15 minutes to 3 hours.

28. The process of claim 20 for preparing a composition comprising unilamellar spherules, said process comprising in said first stage, solubilizing said lipid intended for the formation of said spherules in at least one solvent insoluble in water and packaging the resulting lipid solution in the liquid state in a container at a pressure $P_1$ and at a temperature $\Theta_1$; preparing an aqueous phase containing dissolved substances to be encapsulated in said spherules and packaging the resulting aqueous phase at a pressure $P_2$ and at a temperature $\Theta_2$; and injecting said lipid solution into said aqueous phase at a low rate of flow initially to form droplets such that the solvent in said lipid solution vaporizes when it comes into contact with said aqueous phase, the pressure $P_2$ being less than the pressure $P_1$ and being less than the vapor pressure of the solvent in the droplets at the temperature $\Theta_2$.

29. A method for the therapeutic treatment of the human or animal body comprising administering the composition of claim 1 to a human or animal body.

30. A method for the cosmetic treatment of the human or animal body comprising administering the composition of claim 1 to said human or animal body.

* * * * *